United States Patent
Ellman et al.

(10) Patent No.: US 6,238,388 B1
(45) Date of Patent: May 29, 2001

(54) LOW-VOLTAGE ELECTROSURGICAL APPARATUS

(76) Inventors: Alan G. Ellman; Jon C. Garito, both of 1135 Railroad Ave., Hewlett, NY (US) 11557

( * ) Notice: Subject to any disclaimer, the term of this patent is extended or adjusted under 35 U.S.C. 154(b) by 0 days.

(21) Appl. No.: 09/393,287

(22) Filed: Sep. 10, 1999

(51) Int. Cl.$^7$ ................................... A61B 18/18
(52) U.S. Cl. .................. 606/37; 606/39; 606/40
(58) Field of Search ........................ 606/32, 34, 37, 606/39, 40, 41, 42, 45, 46, 47–50

(56) References Cited

U.S. PATENT DOCUMENTS 4,716,897 * 1/1988 Noguchi et al. ................. 606/34

* cited by examiner

*Primary Examiner*—Lee Cohen
*Assistant Examiner*—R. Kearney

(57) ABSTRACT

Low-power, low-voltage electrosurgical apparatus providing three current unipolar modes whose circuitry for generating the modulation signals needed to implement the three current modes employs no microcontroller but generates the modulation waveforms using a oscillator-binary counter and dual multiplexers, integrated components (ICs) that are of relatively low cost. Safety features can be incorporated by including a timer circuit cooperating with the binary counter to provide power to the IC components and avoid overheating of the apparatus. The oscillator-binary counter component is used to generate at plural outputs plural series of digital pulses at various frequencies, some of the pulse series being used to generate approximate sine-waves that can be employed for the cut/coag and hemo modes, and others of the pulse series being employed to operate a timer, indicator lights, and an audible warning system.

12 Claims, 3 Drawing Sheets

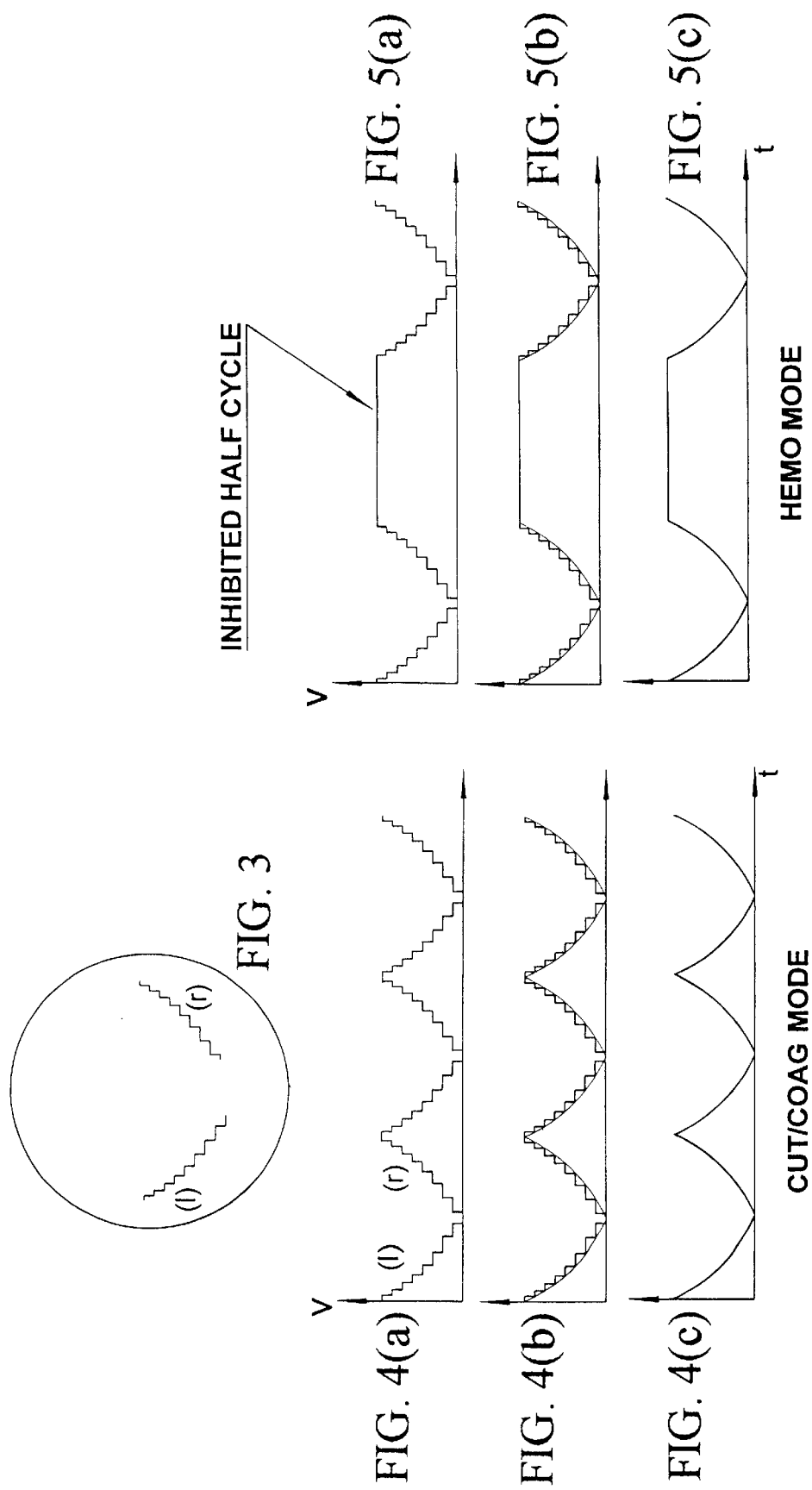

LOW-VOLTAGE ELECTROSURGICAL APPARATUS

The invention is directed to an electrosurgical instrument or apparatus, and in particular to an electrosurgical instrument that operates with a lower output voltage and a lower output power.

BACKGROUND OF INVENTION

Electrosurgical instruments are well known and widely used in the medical, dental, and veterinarian fields. They offer the capability of precision cutting with electrosurgical currents in the megacycle range using a handpiece with needle, ball, or loop electrodes in a unpolar operating mode, or convenient coagulation using a forceps in a bipolar operating model. Eliman International, Inc. makes available an electrosurgical instrument, Model FFPF, which provides on its front panel connectors for receiving the plug of a unipolar handpiece and a ground or indifferent plate, as well as connectors for receiving the plugs of a bipolar forceps.

There are environments in which the electrosurgical apparatus has to satisfy stringent requirements, including but not limited to simple operation, low cost, energy efficient, safe, and user friendly. in addition, it should provide the capability of precision cutting, coagulating, and homeostasis using high radio-frequency (RF) electrical current, preferably of the order of 3.5–4 mHZ, with 4 mHZ being preferred.

We have found that most of these requirements can be satisfied with low power electrosurgical apparatus that includes only unipolar capability provided that the output power is kept low, preferably at or below about 50 watts. The Model FFPF, whose principles are described in some detail in U.S. Pat. No. 3,730,188 ('188), and further in U.S. Pat. No. 4,463,759 ('759), the contents of both of which are fully incorporated herein by reference, had an output of about 100 watts. Moreover, the Model FFPF used electron tubes, which required high voltages to operate and limited the number of user-friendly features that could be incorporated. Other commercial electrosurgical apparatus, also of the high-voltage, high-power type, employed programmable microcontrollers for producing the different current waveforms needed for surgical tissue cutting, for simultaneous cutting and coagulation, and for coagulation (hemostasis) alone, commonly referred to as the cut, cut/coag, and hemo modes, respectively. U.S. Pat. No. 3,730,188 illustrates in FIGS. 5a, 5b and 5c the three modes above described. As will be noted, the cut mode current waveform is a fully-rectified, filly-filtered, continuous wave (CW) carrier at the RF frequency; the cut/coag mode current waveform is a fully-rectified, unfiltered, continuous wave (CW) carrier at the RE frequency; and the hemo mode current waveform is a half-wave rectified, unfiltered, continuous wave (CW) carrier at the RF frequency. The cut/coag and hemo mode currents are commonly referred to as modulated RF currents. The commercial electrosurgical apparatus of the high-voltage, high-power type employing microcontrollers also are more complex, require more electronic components and assembly, and are thus more expensive than the Model FFPF.

SUMMARY OF INVENTION

A principal object of the invention is an electrosurgical apparatus capable of providing optimal RF energy for the three unipolar modes described above but manufacturable at a lower cost.

Another object of the invention is an electrosurgical apparatus capable of providing optimal RF energy for the three unipolar modes described above but characterized by lower output voltage and power.

Still another object of the invention is an electrosurgical apparatus capable of providing optimal RE energy for the three unipolar modes described above but manufacturable at a lower cost yet providing many user-friendly features without the use of a microcontroller.

These objects are achieved in accordance with one aspect of the invention by an electrosurgical apparatus whose circuitry for generating the modulation signals needed to implement the three current modes employs no microcontroller but generates the modulation waveforms using a oscillator-binary counter and dual multiplexers, integrated components (ICs) that are of relatively low cost.

In accordance with another feature of the invention, safety features can be incorporated by including a timer circuit cooperating with the binary counter to provide power to the IC components and avoid overheating of the apparatus.

A feature of the invention is to use the oscillator-binary counter component to generate at plural outputs plural series of digital pulses at various frequencies, some of the pulse series being used to generate approximate sine-waves that can be employed for the cut/coag and hemo modes, and others of the pulse series being employed to operate the timer, indicator lights, and all audible warning system. Thus, many functions are performed by the circuit components thereby minimizing the component count and reducing costs.

Electrosurgical apparatus according to the invention is capable of providing high-quality RF energy at a 3.5–4 mHZ frequency best suited for delicate, precise and quick-healing cutting procedures with low leakage currents using a unipolar handpiece, as well as high-quality modulated RF energy best suited for hemostasis with the unipolar handpiece. In addition, its output RF frequency remains substantially unchanged irrespective of load changes. Moreover, it will provide a controlled duty cycle, i.e., relative times that the RF currents are delivered to a patient versus the times that delivery is interrupted, a feature that was not possible with the Model FFPF.

The various features of novelty which characterize the invention are pointed out with particularity in the claims annexed to and forming a part of of this disclosure. For a better understanding of the invention, its operating advantages and specific objects attained by its use, reference should be had to the accompanying drawings and descriptive matter in which there are illustrated and described the preferred embodiments of the invention, and in which like reference numerals denote the same or similar components.

BRIEF DESCRIPTION OF DRAWINGS

FIG. 3 illustrates parts of a sine-wave to be used to generate the modulation waveforms;

FIGS. 4(a), 4(b) and 4(c) illustrate how a fully rectified half sine-wave modulation waveform can be obtained for one operating mode;

FIGS. 5(a), 5(b) and 5(c) illustrate how a half rectified half sine-wave modulation waveform can be obtained for a different operating mode.

DETAILED DESCRIPTION OF PREFERRED EMBODIMENTS

Electrosurgical apparatus according to the invention is a high frequency, low power output, low-output voltage, allsolid-state electrosurgical apparatus. The construction is unique, simple, energy efficient, safe, and user friendly. It provides the essential operational modes that are most often used in electrosurgical applications. In a preferred form, the unit has a maximum 50 watt output power and provides the capability of precision cutting, coagulating, and homeostasis using, preferably, 4 mHZ frequency electrosurgical currents.

Figure 1:
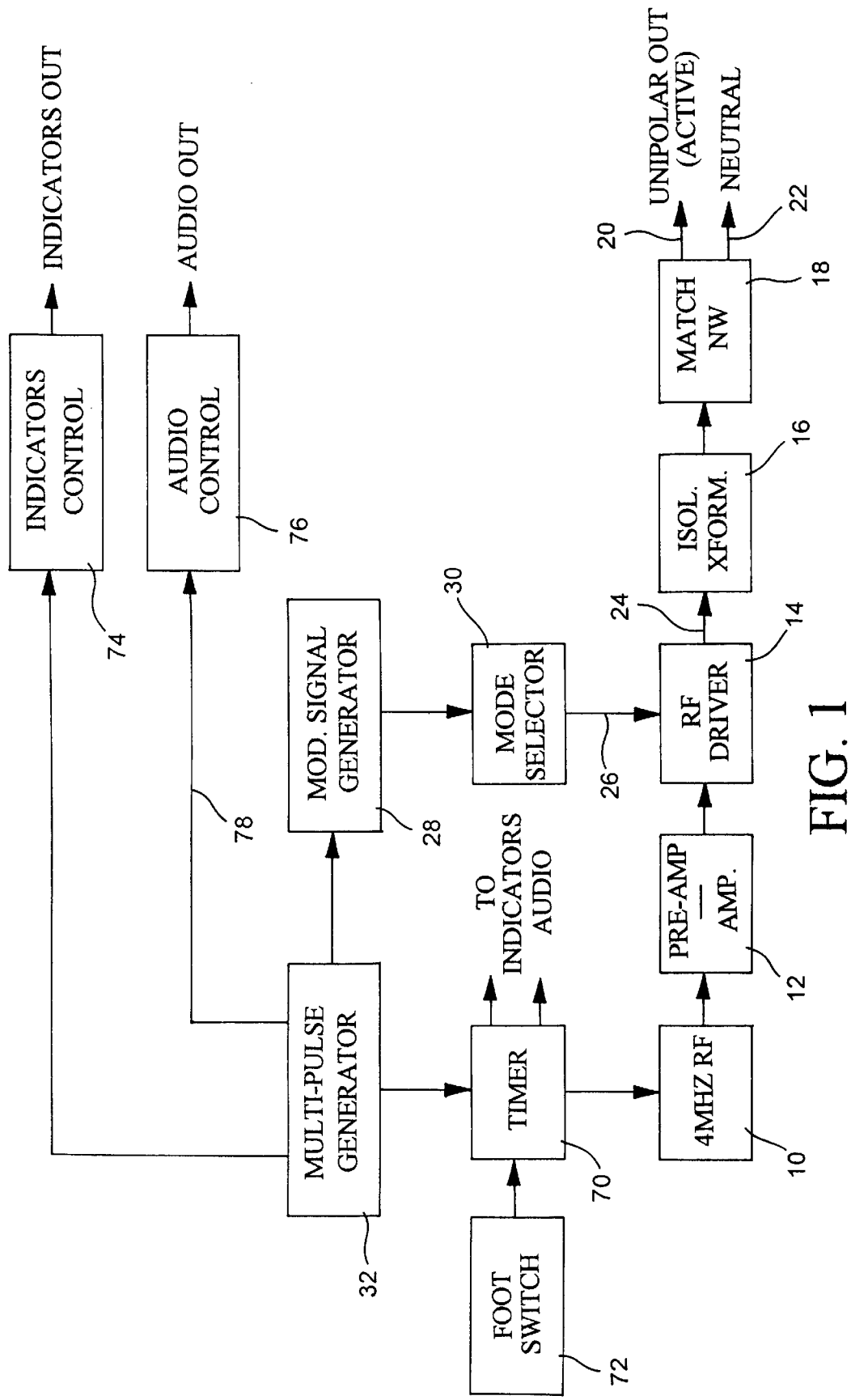
FIG. 1 is a block circuit diagram of one form of electrosurgical apparatus according to the invention.

One form of an electrosurgical apparatus according to the invention comprises several functional interconnected stages as shown in the circuit block diagram of FIG. 1. There are four major functions to be performed; power supply, modulating signal generator, RF generator, and signal modulation, patient isolation and matching. The power supply, RF generator, and signal modulation, patient isolation and matching can for purposes of this application be considered conventional, since any conventional voltage-regulated, RF filtered, stable power source can be substituted, any stable, reliable 4 mHZ RF generator can be substituted, and typical patient isolation is accomplished by an output transformer whose secondary is coupled by way of a matching network to the active lines going to the electrosurgical handpiece and neutral plate. The impedance matching network matches the source impedance to the range of patient impedance. The output power is referenced to ground through an output isolation capacitor (not shown). The impedance matching circuit, which is also commonly known as the patient circuit, is completely isolated from the secondary power circuit by the isolation transformer.

The FIG. 1 block diagram includes these conventional elements to assist in understanding of the invention. The RF carrier is supplied by an RF generator 10, typically a crystal-controlled solid-state oscillator whose output is pre-amplified and then power amplified for driving the RF driver 14. The RF driver may comprise, for example, a power MOS device (not shown) whose body contact is driven by the RF carrier. The MOS source is at ground potential, and its drain circuit is connected to the RF-isolated power supply via the primary of the isolation transformer 16, whose secondary is connected via the matching network 18 to the active 20 and neutral 22 outputs, the active output being accessible by the usual unipolar handpiece and the neutral being typically connected to the ground plate placed in contact with the patient.

The apparatus of the invention generates 3 waveforms to perform the cut, cut/coag, and hemo unipolar functions. These 3 are illustrated in FIGS. 5a, 5b, and 5c of the referenced 188 patent, the cut waveform in FIG. 5a of the patent being the filtered unmodulated RF carrier which would be present at the output 24 of the RF driver 14 (FIG. 1) assuming the modulation is disabled. This pure 4 mHZ signal is sometimes referred to as the CW output. The cut/coag waveform in FIG. 5b of the patent is the full-wave rectified modulated RF carrier which would be present at the output 24 of the RF driver 14 (FIG. 1) assuming a full wave rectified modulation is applied to the modulation input 26 of the RF driver 14, for example, to the drain of the power MOS driver. The hemo waveform in FIG. 5c of the patent is the half-wave rectified modulated RF carrier which would be present at the output 24 of the RF driver 14 (FIG. 1) assuming a half-wave rectified modulation is applied to the modulation input 26 of the RF driver 14, for example, to the drain of the power MOS driver.

The modulating waveforms generator which supplies the full-wave rectified and half-wave rectified modulation is supplied from block 28 via a mode selector switch 30 which can be either a 3-position switch on the front panel of the apparatus or a switch built into the handpiece.

A feature of the invention is the use of a multi-pulse generator 32, preferably in the form of a binary counter/divider, to generate from a simple high frequency oscillator input a plurality of pulse sequences at a number of different rates or frequencies, some of which are integer multiples of each other. More specifically, the counter/divider takes an input frequency and divides it into one or more other frequencies each of which is a predetermined fraction of the input. It typically comprises a number of cascaded flip-flop stages the output frequency of each of which is one-half its input frequency. These trains of pulse sequences perform many different functions, the most important of which include generation of the modulation waveforms. Essentially, the circuit uses digitally controlled analog switches which connect a selected pin to a common output pin. The common output pin of each is connected to a power source through one of a chain of external voltage dividers. Successive selection of the analog switches provides a digital-to-analog function to generate one half of the desired sine function. The waveform shape is determined by the relative values of the resistors forming the voltage divider, while the second half of the half sine-wave is formed by another multiplexer using the same resistors in reverse order. One multiplexer provides a decreasing stepped voltage starting from a maximum voltage of the sine-wave while the other provides an increasing stepped voltage starting from the minimum of the sine-wave. The steps are the same for both. Address selection of the selected pin (channel) of the multiplexors is generated from the oscillator/divider. The divider chain, in conjunction with the oscillator/divider, switches the two multiplexers ON and OFF to generate the downward and upward slopes of the half sinewaves. A further frequency selected by the mode selector inhibits every other half sinusoid to generate the hemo waveform.

Figure 2:
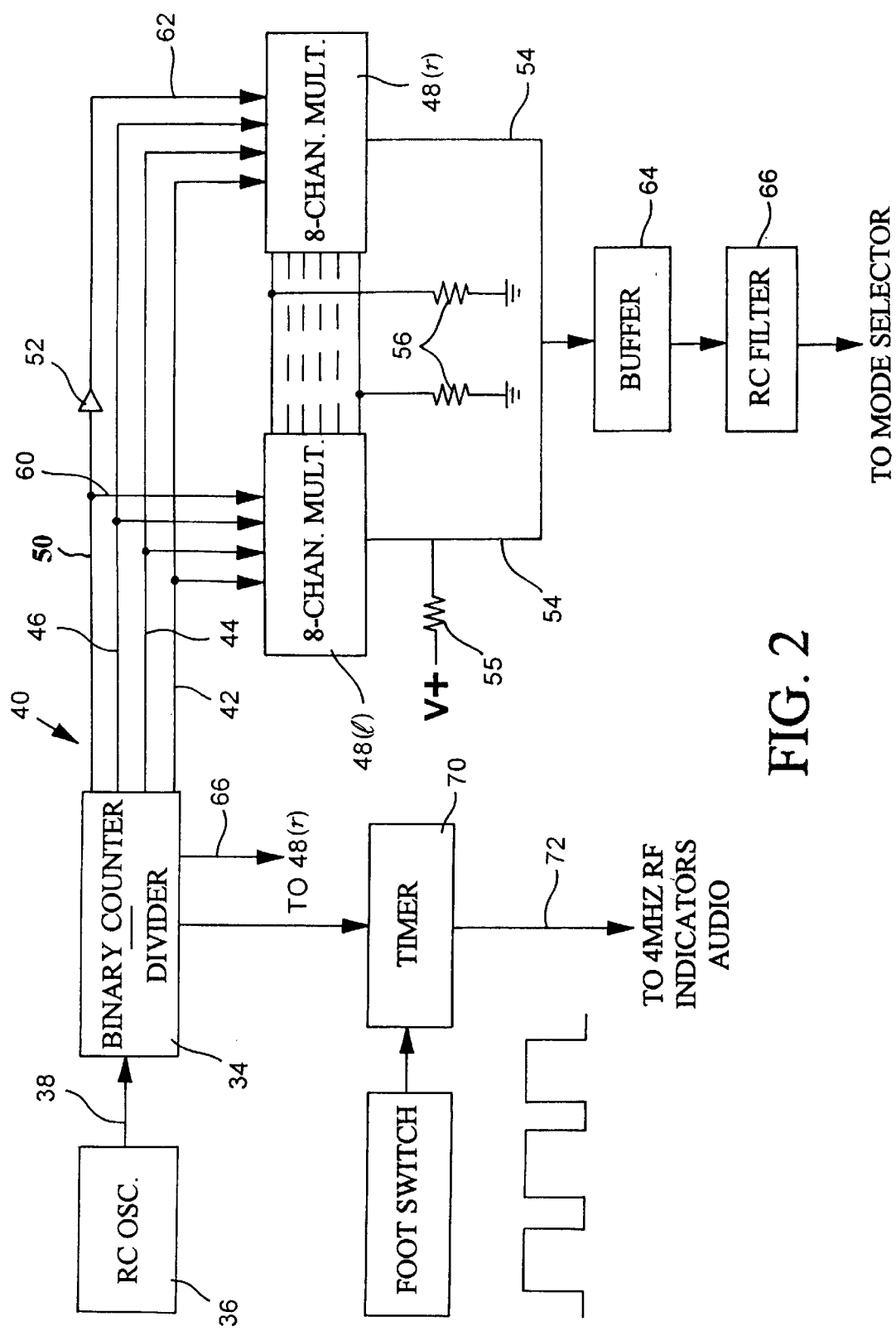
FIG. 2 is a schematic circuit illustrating how the modulation waveforms are obtained.

One form of this digitally-controlled analog switch is illustrated in FIG. 2. A binary counter/divider 34 may be an off-the-shelf component, for example, the CD4060B IC, a CMOS 14-stage ripple-carry binary counter/divider with a built in oscillator. The oscillator designated 36 is shown as a separate component, as it can be separately provided if desired, but is actually included in this particular IC. The oscillator 36 with the addition of suitable RC components generates at its output 38, for example, a 37 kHZ signal. While examples will be given of operating frequencies to better illustrate operation, it will be understood that the invention is not limited to those particular frequencies. The ripple-carry binary counter/divider 34 generates at its output 40 from the 37 kHZ source a number of trains of pulse sequences at lower frequencies which are integer divisors of one another (integers will be used in the examples for simplicity, but it will be understood that, since binary division is involved, each of the signals are in fact exact integer multiples even though the example numbers given appear slightly off); for example, 72, 146, 290, and 580 Hz are multiples of 2 of the preceeding number in the sequence. "Integer divisors" is used herein to mean each number of a series differs from the other numbers by an integer, i.e., any lower number in the series can be obtained by dividing a higher number by an integer. The 146, 290, and 580 Hz pulse frequencies are used to create a 3 digit binary code. For example, since the three pulse sequences are integer divisors, when all pulses have their leading edges aligned, it produces the binary code 1-1-1. When all pulses have out-of-line leading edges, it produces the binary code 0-0-0. When 2 of the pulse trains are aligned, but not the 3rd, then binary signals such as 1-1-0, or 1-0-1, or 0-1-1 are generated. As will be evident, since the pulse trains are integer multiples, a succession of 1 of 8 binary codes will be outputted 40 in sequence. The 72 Hz signal functions as an inhibit signal.

The succession of binary codes is outputted on three lines 42, 44, 46 connected in parallel to a pair of analog multiplexors 48(l) and 48 (r), for example the CD4051B IC. The inhibit signal is applied via line 50 directly to the left multiplexor 48 (l) and via an invertor 52 to the right multiplexor 48 (r). The binary code inputted connects (turns ON) 1 of 8 lines of the multiplexor pairs to a single output lead 54, which is connected to a voltage source V+ and a load resistor 55, and to 1 of 8 resistors 56 of different resistance values, chosen so that 8 successively decreasing/increasing voltage dividers (resistors 55, 56) are created and the output voltage on line 54 has a value that depends on the value of the 1 of 8 resistors to which it is connected. For simplicity, only 2 resistors 56 are shown, but the component in question has 8 outputs (hence the name 8-channel) each of which is connected to 1 of the 8 resistors 56. So, for example, when the binary code 000 is inputted via lines 42, 44, 46, the voltage on line 54 is 5 volts; when the binary code 001 is next inputted, the voltage on line 54 is reduced to 4.4 volts; when the binary code 010 is inputted, the voltage on line 54 is reduced to 3.8 volts; and so on. In this way, by connecting in succession the 8 binary codes to the left multiplexor 48 (l) inputs, the output voltage on line 54 varies in steps from 5 volts to approximately zero. This is illustrated in FIG. 3 at (l) designating the left multiplexor. This function has been carried out while the 72 Hz frequency pulse has been applied via line 50 to the inhibit input 60 of the left multiplexor 48(l). While this 72 Hz pulse is high at the inhibit input 60, the multiplexor 48(l) is enabled. The same 72 Hz frequency pulse is also applied via the invertor 52 to the inhibit input 62 of the right multiplexor 48(r). The invertor 52 inverts the high pulses to low pulses which disables the right multiplexor 48(r). When the 72 Hz frequency pulse terminates, the reverse action takes place. The left multiplexor 48(l) becomes disabled and the right multiplexor 48(r) enabled, and now the output line 54 of the right multiplexor 48(r) as a result of the binary codes inputted shows an increase in voltage of the same steps but reversed to that shown in FIG. 3 at (l), which is shown in the curve labelled (r) in FIG. 3. When the voltages on line 54 are combined over the full cycle, an approximately half sine-wave is generated. This is illustrated in FIG. 4(a), which plots the voltage on line 54 as a function of time t. As will be observed, one-half (l) of the sinewave is produced by the left multiplexor 48(l) and the other half (r) by the right multiplexor 48(r) which have operated in succession as above described.

The output from the multiplexors is passed through a conventional buffer stage 64 and an RC smoothing filter 66 and the output then transmitted to the mode selector switch 30. FIG. 4 (b) illustrates the effect of a smoothing filter on the output waveform, and FIG. 4(c) shows the actual sinewave output that can be used to modulate the 4 mHZ carrier for the cuticoag mode. FIG. 5(a), (b), and (c) show the corresponding outputs at just one of the enabled multiplexors when the other one is disabled. The mode selector 30 applies the desired modulating waveform to the RF driver 14. It will be evident from the foregoing that when, say, the right multiplexor 48(r) is permanently disabled, then the output at line 54 is only the half-wave rectified signal shown in FIG. 5(c). Hence, the hemo mode using the half-wave rectified signal shown in FIG. 5(c) is easily obtained by permanently disabling the right multiplexor 48(r) using a pulse frequency of 36 Hz also obtained from the binary counter/divider 34 at an additional output 66 and supplied to the right multiplexor 48 (r). This additional output is applied when the mode selector switch 30 is switched to its hemo mode.

A timer 70 is used to control operation and provide overload protection. The timer, which is a conventional component, is enabled by a foot switch 72 conventionally used by the surgeon to activate the apparatus. The activation can also be built into the handpiece. See also the referenced '759 patent. When the foot switch is activated, the timer supplies (not shown) operating voltages via lines 72 to the RF generator 10 and also to a set of indicators 74, for example, LEDs, and an audible circuit 76 (FIG. 1). A timer output when enabled turns on a desired indicator, indicating, for example, to the surgeon that the electrosurgical currents are available at the handpiece. If desired, the timer output can also be transmitted via the mode selector switch 30 so that different colored lights are turned ON depending on the selected mode. Simultaneously, the audible circuit 76 can be activated so that the surgeon also receives an audible indication when RF power is available. Conveniently, the audio tone is supplied by another pulse frequency outputted on line 78 from the multipulse generator 32. A suitable frequency is 2 kHz which is also an integer multiple of one of the other frequencies generated.

It is important to prevent overloading (overheating) of the RF oscillator and to prevent possible patient harm. To achieve this function, again a pulse frequency can be derived from the multipulse generator 32 to control the ON/OFF state of the timer. This frequency can again be an integer divisor derived from the oscillator source 36 via the divider 34. The period of such a frequency can be chosen to be about 10 seconds (s), so that the ON time of the timer when activated is limited to the 10s, after which the timer shuts down the operation to avoid overloading. If desired, another frequency can be derived from the divider to automatically turn back ON the timer after, say 30s, which by then will have allowed the circuit to cool down to prevent overheating. In this mode of operation, so long as the foot switch 72 is depressed, the electrosurgical currents will have a duty cycle of 10s ON and 30s OFF. Other duty cycles can obviously be substituted if desired by choosing a different pulse frequency. The operation of the timer is straightforward. A number is programmed in to represent the maximum count of its input pulses, which when reached generates an output control signal that can be used to deactivate, for example, a relay whose contacts supplied power to the various components. The duty cycle can also be readily changed by programming in a different number.

Not shown is a voltage control device for controlling the output power of the electrosurgical currents, with the high power for maximum output preferably selected at 50 watts, the power being controlled down to approximately 5 watts. This output power control is preferably accomplished by controlling the amplitude of the modulating signal that is applied to the drain input of the MOS driver. This has the advantage that it helps stabilize the output frequency.

The apparatus according to the invention provides a stable and controllable source of high frequency electrosurgical energy in all operational modes. Safety and effectiveness are also present. Apparatus built according to the principles desribed herein can be designed to meet the international safety standards specified by the International Electrotechnical Commission.

While the invention has been described in connection with preferred embodiments, it will be understood that modifications thereof within the principles outlined above will be evident to those skilled in the art and thus the invention is not limited to the preferred embodiments but is intended to encompass such modifications.

What is claimed is:

1. Electrosurgical apparatus comprising:

a) an active output for connection to an electrosurgical handpiece,
   b) an RF generator for generating an RF carrier for producing first electrosurgical currents capable of an electrosurgical cut mode of operation,
   c) first means for generating first and second modulating currents, the first modulating currents when combined with the RF carrier producing second electrosurgical currents capable of a cut/coag mode of operation, the second modulating currents when combined with the RF carrier producing third electrosurgical currents capable of an electrosurgical hemo mode of operation,
   d) selector means for selectively combining the RF carrier with the first or the second modulating currents or with neither of the first or second modulating currents to selectively produce electrosurgical currents capable of the cut, cut/coag, or hemo modes of operation, respectively, said means for selectively combining being connected to the active output to provide at the output the electrosurgical currents capable of the selected mode,
   e) said first means comprising:
      i) second means for generating multiple trains of pulses at frequencies that are integer divisors of each other and for generating from the multiple trains of pulses a sequence of address codes,
      ii) third means comprising a digitally controlled analog switch having plural channels for receiving and being responsive to the address codes for generating an approximate sine-wave capable of being used to produce the first and second modulating currents.

2. Electrosurgical apparatus as claimed in claim 1, wherein the third means comprises means in response to the means for generating multiple trains of pulses for selectively generating at an output a stepped signal that varies from a maximum to a minimum and from the minimum to the maximum.

3. Electrosurgical apparatus comprising:

a) an active output for connection to an electrosurgical handpiece,
   b) an RF generator for generating an RF carrier for producing first electrosurgical currents capable of an electrosurgical cut mode of operation,
   c) first means for generating first and second modulating currents, the first modulating currents when combined with the RF carrier producing second electrosurgical currents capable of a cut/coag mode of operation, the second modulating currents when combined with the RF carrier producing third electrosurgical currents capable of an electrosurgical hemo mode of operation,
   d) selector means for selectively combining the RF carrier with the first or the second modulating currents or with neither of the first or second modulating currents to selectively produce electrosurgical currents capable of the cut, cut/coag, or hemo modes of operation, respectively, said means for selectively combining being connected to the active output to provide at the output the electrosurgical currents capable of the selected mode,
   e) said first means comprising:
      i) an oscillator for generating a waveform at a first frequency,
      ii) a binary counter/divider for receiving the waveform at the first frequency and producing from it pulsed sequences at at least second, third, and fourth frequencies, the second, third and fourth frequencies being integer divisors of the first frequency,
      iii) a digitally controlled analog switch having plural channels each having an output connected via a voltage source to a different load, the digitally-controlled analog switch receiving and being responsive to the second, third and fourth frequencies for activating one of the plural channels at a time in sequence to connect in sequence the different loads,
      iv) means for combining the voltage levels appearing across the different loads to generate an approximate sine-wave capable of being used to produce the first and second modulating currents.

4. Electrosurgical apparatus as claimed in claim 3, wherein the second, third, and fourth frequencies constitute a 1 of 8 binary code.

5. Electrosurgical apparatus as claimed in claim 3, further comprising a plurality of different impedances connectable to the analog switch output, said impedances having values such that they are capable of forming voltage dividers which cause the analog switch output to acquire voltages varying in steps between maximum and minimum values.

6. Electrosurgical apparatus as claimed in claim 3, further comprising a smoothing filter connected to the analog switch output.

7. Electrosurgical apparatus as claimed in claim 3, wherein the means for combining the voltage levels includes means for combining sequences of half sine-waves to produce a fully rectified sine-wave serving as the first modulating current.

8. Electrosurgical apparatus as claimed in claim 3, wherein the means for combining the voltage levels includes means for combining sequences of alternate half sine-waves to produce a half-wave rectified sine-wave serving as the second modulating current.

9. Electrosurgical apparatus as claimed in claim 3, further comprising a timer operable to receive a frequency that is an integer divisor of the first frequency for generating an ON-OFF duty cycle for controlling operation of the apparatus.

10. Electrosurgical apparatus as claimed in claim 3, further comprising indicators operable to receive a frequency that is an integer divisor of the first frequency for indicating various functions of the apparatus.

11. Electrosurgical apparatus as claimed in claim 3, further comprising an audio circuit operable to receive a frequency that is an integer divisor of the first frequency for audibly indicating various functions of the apparatus.

12. In combination:

(i) an electrosurgical handpiece;
   (ii) low power electrosurgical apparatus comprising:
      A) an active output for connection to the electrosurgical handpiece,
      B) an RF generator for generating an RF carrier for producing first electrosurgical currents capable of an electrosurgical cut mode of operation,
      C) first means for generating first and second modulating currents, the first modulating currents when combined with the RF carrier producing second electrosurgical currents capable of a cut/coag mode of operation, the second modulating currents when combined with the RF carrier producing third electrosurgical currents capable of an electrosurgical hemo mode of operation, D) selector means for selectively combining the RF carrier with the first or the second modulating currents or with neither of the first or second modulating currents to selectively produce electrosurgical currents capable of the cut, cut/coag, or hemo modes of operation, respectively, said means for selectively combining being connected to the active output to provide at the output the electrosurgical currents capable of the selected mode, E) said first means comprising:
   a) an oscillator for generating a waveform at a first frequency,
   b) a binary counter/divider for receiving the waveform at the first frequency and producing from it pulsed sequences at at least second, third, and fourth frequencies, the second, third and fourth frequencies being integer divisors of the first frequency,
   c) a digitally controlled analog switch having plural channels each having an output connected via a voltage source to a different load, the digitally-controlled analog switch receiving and being responsive to the second, third and fourth frequencies for activating one of the plural channels at a time in sequence to connect in sequence the different loads,
   d) means for combining the voltage levels appearing across the different loads to generate an approximate sine-wave capable of being used to produce the first and second modulating currents;

(iii) the first, second and third electrosurgical currents capable of the cut, cut/coag, or hemo modes of operation, respectively, being generated without benefit of a microcontroller.

* * * * *